(12) United States Patent
Uchiyama et al.

(10) Patent No.: US 8,603,939 B2
(45) Date of Patent: Dec. 10, 2013

(54) AMIDE COMPOUND PRODUCTION CATALYST, AND PROCESS FOR PRODUCTION OF AMIDE COMPOUND

(75) Inventors: Takako Uchiyama, Niigata (JP); Shinyou Shirai, Niigata (JP); Yoshikazu Shima, Niigata (JP); Masaki Takemoto, Niigata (JP); Genki Nogami, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 13/582,182

(22) PCT Filed: Mar. 4, 2011

(86) PCT No.: PCT/JP2011/055108
§ 371 (c)(1),
(2), (4) Date: Sep. 25, 2012

(87) PCT Pub. No.: WO2011/108717
PCT Pub. Date: Sep. 9, 2011

(65) Prior Publication Data
US 2013/0041179 A1    Feb. 14, 2013

(30) Foreign Application Priority Data
Mar. 4, 2010    (JP) .................................. 2010-047916

(51) Int. Cl.
*B01J 23/34*    (2006.01)
*C07C 231/06*    (2006.01)

(52) U.S. Cl.
USPC ............................. 502/324; 564/126; 564/128

(58) Field of Classification Search
None
See application file for complete search history.

(56) References Cited

U.S. PATENT DOCUMENTS

| | | | |
|---|---|---|---|
| 4,987,256 A * | 1/1991 | Ebata et al. ................... | 564/126 |
| 5,276,185 A | 1/1994 | Karasawa et al. | |
| 5,756,842 A | 5/1998 | Tanaka et al. | |
| 7,704,917 B2 | 4/2010 | Matsuda et al. | |
| 7,714,166 B2 | 5/2010 | Nogami et al. | |
| 2009/0036301 A1 | 2/2009 | Matsuda et al. | |
| 2009/0143616 A1 | 6/2009 | Nogami et al. | |
| 2012/0149933 A1 | 6/2012 | Yamamoto et al. | |

FOREIGN PATENT DOCUMENTS

| | | |
|---|---|---|
| JP | 47-4068 A | 2/1972 |
| JP | 52-222 A | 1/1977 |
| JP | 63-57534 A | 3/1988 |
| JP | 63-57535 A | 3/1988 |
| JP | 3-93761 A | 4/1991 |
| JP | 5-170720 A | 7/1993 |
| JP | 6-269666 A | 9/1994 |
| JP | 6-340602 A | 12/1994 |
| JP | 7-228560 A | 8/1995 |
| JP | 9-19637 A | 1/1997 |
| JP | 9-24275 A | 1/1997 |
| JP | 9-188656 A | 7/1997 |
| JP | 11-319558 A | 11/1999 |
| WO | 2007/007633 A1 | 1/2007 |
| WO | 2007/037082 A1 | 4/2007 |

OTHER PUBLICATIONS

"A method of adding an aqueous solution of potassium permanganate to an aqueous solution of manganese sulfate", Zeit Anorg. Allg. Chem., 1961, vol. 309, pp. 1-32 and 121-150.
O. Mancera et al, "A method of reducing permanganate with hydrohalic acid", Journal Chem. Soc., 1953, vol. 2189.

* cited by examiner

*Primary Examiner* — Brian J Davis
(74) *Attorney, Agent, or Firm* — Greenblum & Bernstein, P.L.C.

(57) ABSTRACT

The present provides a high-efficiency amide compound production catalyst to be used in producing an amide compound through hydration of a nitrile compound and a production method using it. The amide compound production catalyst is for producing an amide compound through reaction of a nitrile compound and water, and comprises a manganese oxide catalyst containing bismuth and further containing yttrium or vanadium. The method for producing an amide compound comprises reacting a nitrile compound and water in a liquid phase in the presence of the amide compound production catalyst.

13 Claims, No Drawings

US 8,603,939 B2

AMIDE COMPOUND PRODUCTION CATALYST, AND PROCESS FOR PRODUCTION OF AMIDE COMPOUND

TECHNICAL FIELD

The present invention relates to an amide compound production catalyst for use in production of an amide compound through reaction of a nitrile compound and water in a liquid phase, and to a method for producing an amide compound; and in particular, the present invention relates to an amide compound production catalyst with which an amide compound can be produced with high efficiency and to a method for producing an amide compound.

BACKGROUND ART

A hydroxycarboxylic acid amide to be obtained through hydration of acetone cyanhydrin, which is a type of a nitrile compound, is an important compound as a starting material for production of hydroxycarboxylates or unsaturated carboxylates. Therefore, development of a high-performance nitrile hydration catalyst could bring about a significant industrial meaning; and heretofore, as a high-activity, high-selectivity and long-life catalyst for nitrile hydration, a hydration catalyst that comprises a manganese oxide as the main ingredient thereof and its production method, as well as an amide compound production method using the hydration catalyst have been disclosed (for example, see Patent References 1 to 7).

Of those, Patent Reference 2 discloses addition of Zn, Cd or Hg to a manganese oxide catalyst to enhance the catalytic activity; Patent Reference 3 discloses addition of Zr, V, or Sn thereto; Patent Reference 4 discloses addition of an element selected from elements of Groups 3, 4, 5, 13, 14, 15, 16, 8, 9 and 10 of the Periodic System thereto; and Patent Reference 5 discloses addition of Nb, Ta, Cr, Mo, W, Si, Ge, Pb, As or Sb thereto.

However, in case where these catalysts are used industrially, the catalytic activity could not be sufficient, and further activity enhancement is desired.

CITATION LIST

Patent Reference

Patent Reference 1: JP-A 47-4068
Patent Reference 2: JP-A 63-57534
Patent Reference 3: JP-A 3-93761
Patent Reference 4: JP-A 5-170720
Patent Reference 5: JP-A 6-340602
Patent Reference 6: JP-A 11-319558
Patent Reference 7: WO07/007633

SUMMARY OF THE INVENTION

Problems that the Invention is to Solve

An object of the present invention is to develop a catalyst effective in production of an amide compound through hydration of a nitrile compound. In hydration of a nitrile compound according to the above-mentioned conventional art, the reaction efficiency could not be sufficient on an industrial scale, and it is expected to use a high-performance catalyst to construct a more high-efficiency reaction system.

Means for Solving the Problems

The present inventors have assiduously studied for the purpose of solving the above-mentioned problems and, as a result, have found that, when at least one compound containing yttrium or vanadium is further added to a catalyst comprising a manganese oxide as the main ingredient thereof, in addition to adding a bismuth-containing compound thereto, then the catalytic activity can be enhanced. Specifically, the present invention relates to the following:

1. An amide compound production catalyst for producing an amide compound through reaction of a nitrile compound and water, which comprises a manganese oxide catalyst containing bismuth and further containing yttrium or vanadium.
2. The amide compound production catalyst of the above 1, wherein the atomic ratio of bismuth/manganese is from 0.001 to 0.1.
3. The amide compound production catalyst of the above 1 or 2, wherein the atomic ratio of yttrium/manganese is from 0.001 to 0.1.
4. The amide compound production catalyst of the above 1 or 2, wherein the atomic ratio of vanadium/manganese is from 0.001 to 0.1.
5. The amide compound production catalyst of the above 1, wherein the atomic ratio of (bismuth+vanadium)/manganese is from 0.002 to 0.040.
6. The amide compound production catalyst according to above 1, wherein the atomic ratio of bismuth/(bismuth+vanadium) is from 0.05 to 0.95.
7. A method for producing an amide compound, which comprises reacting a nitrile compound and water in a liquid phase in the presence of the amide compound production catalyst of anyone of the above 1 to 6.
8. The amide compound production method of the above 7, wherein the nitrile compound is an acetone cyanhydrin.

Advantage of the Invention

According to the present invention, there is obtained a high-activity nitrile hydration catalyst. When the catalyst is used, for example, a hydroxycarboxylic acid amide can be produced from acetone cyanhydrin with high efficiency, and the industrial meaning thereof is extremely great.

Mode for Carrying out the Invention

The present is described in detail hereinunder. For the nitrile hydration catalyst of the present, which comprises a manganese oxide as the main ingredient thereof and which contains bismuth and further contains, in addition thereto, a third metal ingredient (yttrium or vanadium), manganese dioxide is mainly used as the manganese oxide therein, and manganese dioxide is a manganese oxide generally falling between $MnO_{1.7}$ and $MnO_2$. It is known that manganese dioxide can have various crystal structures, and owing to phase transition between various phases and crystallinity change to occur therein, the structures are extremely complicated and of great variety.

The manganese oxide for use in the present invention can be prepared according to various known methods; and for example, those prepared according to a method of reducing a heptavalent manganese, those prepared according to a method of oxidizing a divalent manganese, or those prepared according to a method of combining those preparation methods are preferably used here. In case where manganese oxide prepared by reducing a heptavalent manganese is used, the preparation method includes a method of reducing a permanganic acid compound at 20 to 100° C. under a pernutral or alkaline condition (Zeit. Anorg. Allg. Chem., 309, pp. 1-32 and pp. 121-150 (1961)), a method of adding an aqueous solution of potassium permanganate to an aqueous solution of manganese sulfate (O. Mancera, G. Rosenkranz, and F. Sondheimer, J. Chem. Soc., 2189, (1953)), a method of reducing a permanganate with a hydrohalic acid (JP-A 63-57535), a method of reducing a permanganate with a polycarboxylic acid or a polyalcohol (JP-A 9-24275, 9-19637), or a method of reducing a permanganate with, hydrazine a hydroxycarboxylic acid or its salt (JP-A 6-269666); and those prepared according to any of these methods are preferably used here. On the other hand, in case where manganese oxide prepared through oxidization of a divalent manganese is used, preferred is use of those prepared according to a method of thermally decomposing manganese nitrate or manganese carbonate, or a method of electrolytically oxidizing an aqueous solution of manganese sulfate.

The oxide catalyst of the present invention, which comprises a manganese oxide as the main ingredient thereof and contains bismuth and further contains, in addition thereto, a third metal ingredient (yttrium or vanadium), can be prepared by adding a compound containing the metal element to be added, during or after preparation of manganese oxide according to the above-mentioned method. For the addition method, employable here is any method of immersion, adsorption, kneading, coprecipitation, etc. Preferably, the metal compound to be added is dissolved in a solvent and added to the system. For example, a mixture solution containing bismuth oxide, a third metal compound (yttrium compound or vanadium compound) and a divalent manganese compound is mixed with a solution containing potassium permanganate, then reacted and ripened for completing the reaction, and thereafter the formed slurry precipitate is filtered and washed for solid-liquid separation to give the intended oxide catalyst that contains manganese, bismuth and the third metal ingredient (yttrium or vanadium). For controlling the crystal structure and the specific surface area of the catalyst, and the content of bismuth and the third metal ingredient (yttrium or vanadium) in the catalyst, the proportion of the hexavalent and divalent manganese, the concentration of the solution of the starting material, the temperature in mixing, the temperature in ripening, and the time for the treatment may be suitably selected.

As the divalent manganese source for use for the catalyst preparation, selected is a water-soluble salt, and above all, a sulfate is especially preferred. As the hexavalent manganese source, also selected is a water-soluble salt, and above all, potassium permanganate is especially preferred.

As the third metal ingredient (yttrium or vanadium) source, preferred is a water-soluble salt or halide, and above all, a sulfate, a nitrate, a metal acid salt and a chloride are especially preferred. As the bismuth source, usable is not only a water-soluble salt such as bismuth sulfate or bismuth nitrate but also bismuth oxide.

The amount of the bismuth compound to be added is generally from 0.0001 to 0.1 in terms of the atomic ratio of bismuth/manganese, but preferably from 0.001 to 0.1, more preferably from 0.002 to 0.05. On the other hand, the amount of the third metal ingredient yttrium to be added is generally from 0.0001 to 0.1 in terms of the atomic ratio of yttrium/manganese, but preferably from 0.001 to 0.1, more preferably from 0.002 to 0.05. The amount of the other third metal ingredient vanadium to be added is generally from 0.0001 to 0.1 in terms of the atomic ratio of vanadium/manganese, but preferably from 0.001 to 0.1, more preferably from 0.002 to 0.05.

The atomic ratio of (bismuth+vanadium)/manganese is generally from 0.002 to 0.040, but preferably from 0.003 to 0.030, more preferably from 0.004 to 0.022, even more preferably from 0.005 to 0.020; and the atomic ratio of bismuth/(bismuth+vanadium) is generally from 0.05 to 0.95, but preferably from 0.10 to 0.90, more preferably from 0.15 to 0.85, even more preferably from 0.20 to 0.80, most preferably from 0.25 to 0.75.

The nitrile compound to be used in the production method of the present invention includes cyanhydrins to be produced with ease from various types of carbonyl group-having compounds and hydrogen cyanide in the presence of a basic catalyst; and as a concrete cyanhydrin, there is exemplified acetone cyanhydrin.

The hydration using the manganese oxide catalyst of the present invention is attained in a liquid phase, generally in a system with excessive water therein. Specifically, the proportion of the nitrile compound in the starting material liquid is from 5 to 80% by weight, preferably from 20 to 60% by weight, and therefore, the proportion of water therein is from 20 to 95% by weight, preferably from 40 to 80% by weight. The reaction temperature is within a range of from 10 to 100° C., preferably from 20 to 90° C. At a temperature lower than the range, the reaction speed may be low; but at a temperature higher than the range, the amount of the side product to be produced may increase unfavorably. The reaction pressure may be reduced pressure, atmospheric pressure or increased pressure so far as the reaction material could keep a liquid phase at the reaction temperature under the pressure.

In case where a ketone cyanhydrin is used as the nitrile compound, preferably, a ketone that is the starting material for the ketone cyanhydrin is added to the system in an amount of from 10 to 300% by weight of the nitrile compound, for the purpose of preventing the ketone cyanhydrin from decomposing. For example, in case where an acetone cyanhydrin is used as the starting material, preferably, acetone is added to the starting material liquid, as disclosed in JP-A 52-222.

In the present invention, the nitrile compound hydration is attained in a fixed bed system where the manganese oxide catalyst prepared in the manner as above is used as a shaped compact thereof, or in a suspended bed system where the catalyst is used as a powder, granules or microballoons thereof. In the catalyst fixed bed system, the nitrile compound and water and others for the starting material liquid may be previously mixed or they may be individually fed in the reactor. The residence time for the reaction liquid to be held in the reactor may be suitably settled so that the nitrile compound could be converted into the intended amide compound at a high conversion ratio and at a high selectivity ratio. The production liquid containing the amide compound formed through the reaction is purified through distillation, thereby giving the intended high-purity amide compound. Next, the method of the present invention is described more concretely with reference to Examples; however, the scope of the present invention should not be limited by these Examples.

EXAMPLES

Next, the method of the present invention is described more concretely with reference to Examples; however, the scope of the present invention should not be limited by these Examples.

(1-1) Preparation of Catalyst

Catalyst 1

62.96 g (0.398 mol) of potassium permanganate was dissolved in 217.54 ml of water, and while the resulting liquid was kept stirring at 85° C., immediately added thereto was a liquid that had been prepared by dissolving 56.36 g (0.333 mol) of manganese sulfate monohydrate and 2.45 g (0.004 mol) of yttrium sulfate octahydrate in 215.48 ml of water followed by further mixing the solution with 99.94 g (1.019 mol) of concentrated sulfuric acid and kept at 55° C. After the addition, the reaction mixture was ripened by stirring at 70° C. for 2 hours, and further at 90° C. for 4 hours; and thereafter a liquid prepared by suspending 1.90 g (0.004 mol) of bismuth(III) oxide in 440 ml of water was immediately added to the reaction mixture. After this was stirred at room temperature for 30 minutes, the formed precipitate was taken out through filtration and washed until the electroconductivity of the wash waste could reach 300 µS/cm, thereby giving a precipitate cake.

The obtained cake was molded through an extrusion molding machine (cylinder diameter 35 mm$\phi$, nozzle diameter 1.5 mm$\phi$×24 holes, aperture 4.4%, hydraulic system) and dried with a stationary drier at 110° C. for 16 hours thereby giving about 60 g of a molded catalyst with a size of 1.0 mm$\phi$×3 to 7 mm.

Catalyst 2

A catalyst produced in the same manner as that for the catalyst 1 except that 1.85 g (0.008 mol) of vanadium(IV) oxysulfate 3.7-hydrate was added in place of yttrium sulfate octahydrate.

Comparative Catalyst 1

A catalyst produced in the same manner as that for the catalyst 1 except that yttrium sulfate octahydrate was not added.

Comparative Catalyst 2

A catalyst produced in the same manner as that for the catalyst 1 except that 2.93 g (0.004 mol) of lanthanum sulfate nonahydrate was added in place of yttrium sulfate octahydrate.

Comparative Catalyst 3

A catalyst produced in the same manner as that for the catalyst 1 except that 3.25 g (0.008 mol) of cerium sulfate tetrahydrate was added in place of yttrium sulfate octahydrate.

Comparative Catalyst 4

A catalyst produced in the same manner as that for the catalyst 1 except that 3.08 g (0.004 mol) of erbium sulfate octahydrate was added in place of yttrium sulfate octahydrate.

Comparative Catalyst 5

A catalyst produced in the same manner as that for the catalyst 1 except that 3.13 g (0.004 mol) of ytterbium sulfate was added in place of yttrium sulfate octahydrate.

Comparative Catalyst 6

A catalyst produced in the same manner as that for the catalyst 1 except that 36.43 g (0.008 mol) of aqueous 30 wt. % titanium sulfate solution was added in place of yttrium sulfate octahydrate.

Comparative Catalyst 7

A catalyst produced in the same manner as that for the catalyst 1 except that 2.90 g (0.008 mol) of zirconium sulfate tetrahydrate was added in place of yttrium sulfate octahydrate.

Comparative Catalyst 8

A catalyst produced in the same manner as that for the catalyst 1 except that 2.16 g (0.008 mol) of ammonium(VII) perrhenate was added in place of yttrium sulfate octahydrate.

Comparative Catalyst 9

A catalyst produced in the same manner as that for the catalyst 1 except that 2.27 g (0.008 mol) of iron(II) sulfate heptahydrate was added in place of yttrium sulfate octahydrate.

Comparative Catalyst 10

A catalyst produced in the same manner as that for the catalyst 1 except that 1.66 g (0.004 mol) of iron(III) sulfate was added in place of yttrium sulfate octahydrate.

Comparative Catalyst 11

A catalyst produced in the same manner as that for the catalyst 1 except that 2.26 g (0.008 mol) of cobalt sulfate heptahydrate was added in place of yttrium sulfate octahydrate.

Comparative Catalyst 12

A catalyst produced in the same manner as that for the catalyst 1 except that 2.14 g (0.008 mol) of nickel sulfate hexahydrate was added in place of yttrium sulfate octahydrate.

Comparative Catalyst 13

A catalyst produced in the same manner as that for the catalyst 1 except that 2.04 g (0.008 mol) of copper(II) sulfate pentahydrate was added in place of yttrium sulfate octahydrate.

Comparative Catalyst 14

A catalyst produced in the same manner as that for the catalyst 1 except that 1.25 g (0.004 mol) of silver(I) sulfate was added in place of yttrium sulfate octahydrate.

Comparative Catalyst 15

A catalyst produced in the same manner as that for the catalyst 1 except that 2.31 g (0.008 mol) of zinc sulfate heptahydrate was added in place of yttrium sulfate octahydrate.

Comparative Catalyst 16

A catalyst produced in the same manner as that for the catalyst 1 except that 2.53 g (0.004 mol, calculated as n=16) of aluminium sulfate n-hydrate (n=14 to 18) was added in place of yttrium sulfate octahydrate.

Comparative Catalyst 17

A catalyst produced in the same manner as that for the catalyst 1 except that 3.02 g (0.008 mol) of aluminium nitrate nonahydrate was added in place of yttrium sulfate octahydrate.

Comparative Catalyst 18

A catalyst produced in the same manner as that for the catalyst 1 except that 3.22 g (0.008 mol, calculated as n=8) of gallium nitrate n-hydrate (n=7 to 9) was added in place of yttrium sulfate octahydrate.

Comparative Catalyst 19

A catalyst produced in the same manner as that for the catalyst 1 except that 2.08 g (0.004 mol) of indium sulfate was added in place of yttrium sulfate octahydrate.

Comparative Catalyst 20

A catalyst produced in the same manner as that for the catalyst 1 except that 2.03 g (0.004 mol) of thallium sulfate was added in place of yttrium sulfate octahydrate.

Comparative Catalyst 21

A catalyst produced in the same manner as that for the catalyst 1 except that 3.12 g (0.0145 mol) of tin sulfate was added in place of yttrium sulfate octahydrate.

Comparative Catalyst 22

A catalyst produced in the same manner as that for the catalyst 1 except that 2.62 g (0.008 mol) of potassium tungstate was added into an aqueous solution of potassium permanganate in place of yttrium sulfate octahydrate.

(1-2) Determination of Acetone Cyanhydrin Hydration Performance

Catalysts 1, 2, Comparative Catalysts 1 to 22

The activity of each catalyst for acetone cyanhydrin hydration was evaluated from the yield of α-hydroxyisobutyric acid amide (HBD) according to the method mentioned below. The catalyst prepared according to the above-mentioned method was folded into a length of from 3 to 4 mm, and 2.88 g thereof was filled into a jacketed glass reactor having an inner diameter of 10 mmϕ. Hot water at 60° C. was kept running through the jacket. A starting material liquid prepared by mixing 40% by weight of acetone cyanhydrin, 10% by weight of acetone and 50% by weight of water was introduced into the reactor tube at a flow rate of 30 g/hr, and at the same time, air was introduced thereinto at a rate of 19 mL/hr. After 2 days and 9 days from the start of the reaction, the reaction liquid discharged out of the reactor was analyzed through high-performance liquid chromatography, thereby determining the yield of HBD and the amount of HBD produced before the yield of HBD lowered to 55%. Here, the amount of HBD produced before the yield of HBD lowered to 55% means the amount of HBD production at a yield of 55% on the primary line derived from the amount of HBD production and the yield thereof at every one day from day 2 to day 9 from the start of the reaction. The found data are shown in Table 1 and Table 2.

Mn—Bi+Various Metal Catalyst Activity Evaluation Result (1)

TABLE 1

| Catalyst | Total Amount of HBD Production (g) | | | | | | | | Yield (%) | | | | | | | |
|---|---|---|---|---|---|---|---|---|---|---|---|---|---|---|---|---|
| | Day 2 | Day 3 | Day 4 | Day 5 | Day 6 | Day 7 | Day 8 | Day 9 | Day 2 | Day 3 | Day 4 | Day 5 | Day 6 | Day 7 | Day 8 | Day 9 |
| Catalyst 1 | 128 | 202 | — | 361 | 424 | 495 | — | 626 | 66.6 | 66.2 | — | 64.2 | 63.0 | 62.2 | 59.7 | 59.7 |
| Catalyst 2 | 125 | 199 | — | 359 | 423 | 493 | 571 | 627 | 66.2 | 66.0 | — | 62.8 | 62.9 | 62.0 | 60.7 | 60.1 |
| Comparative Catalyst 1 | 124 | 193 | — | 328 | — | 462 | 527 | 590 | 61.6 | 61.7 | — | 59.0 | — | 56.7 | 55.2 | 54.4 |
| Comparative Catalyst 2 | 120 | 193 | — | 348 | 407 | 473 | 544 | 595 | 63.6 | 64.0 | — | 60.4 | 58.9 | 57.8 | 55.3 | 53.9 |
| Comparative Catalyst 3 | 108 | 163 | — | 290 | 353 | 392 | 440 | 492 | 56.9 | 55.6 | — | 49.9 | 46.4 | 45.5 | 43.0 | 40.9 |
| Comparative Catalyst 4 | 132 | — | 277 | — | 409 | 476 | 535 | — | 63.7 | — | 63.6 | — | 61.1 | 58.6 | 57.5 | — |
| Comparative Catalyst 5 | 143 | 201 | — | 349 | 432 | — | 544 | 611 | 64.9 | 64.1 | — | 62.5 | 60.9 | — | 57.6 | 57.2 |
| Comparative Catalyst 6 | 109 | 170 | 224 | 290 | — | 389 | 454 | 495 | 54.6 | 53.0 | 52.2 | 50.9 | — | 46.8 | 44.8 | 43.3 |
| Comparative Catalyst 7 | 119 | 199 | — | 335 | 410 | 468 | 535 | 595 | 60.0 | 60.5 | — | 58.8 | 58.6 | 57.0 | 56.8 | 55.1 |
| Comparative Catalyst 8 | — | 214 | — | 359 | 442 | — | 557 | — | 65.5 | — | 63.2 | 61.5 | — | 59.1 | — | |
| Comparative Catalyst 9 | 126 | 190 | 278 | — | 394 | 454 | 524 | — | 61.9 | 60.6 | 59.6 | — | 58.0 | 55.9 | 55.6 | — |
| Comparative Catalyst 10 | 134 | 199 | 261 | — | 411 | 491 | 538 | 598 | 66.7 | 66.5 | 65.3 | — | 62.6 | 60.5 | 58.9 | 57.5 |
| Comparative Catalyst 11 | 133 | 189 | — | — | 376 | 442 | 502 | 562 | 61.7 | 61.0 | — | — | 55.0 | 54.1 | 52.5 | 50.5 |
| Comparative Catalyst 12 | 124 | 221 | — | 348 | 423 | 483 | 548 | 610 | 64.4 | 64.2 | — | 61.1 | 60.0 | 58.0 | 56.8 | 55.6 |
| Comparative Catalyst 13 | 67 | 107 | — | 158 | — | — | — | — | 33.1 | 30.6 | — | 22.9 | — | — | — | — |
| Comparative Catalyst 14 | 142 | 211 | 305 | — | 427 | 491 | 566 | 624 | 68.2 | 65.7 | 64.3 | — | 60.7 | 59.2 | 57.2 | 55.5 |
| Comparative Catalyst 15 | 133 | 205 | 281 | 353 | — | 488 | 546 | 618 | 66.5 | 65.2 | 63.1 | 63.1 | — | 59.6 | 58.0 | 56.6 |
| Comparative Catalyst 16 | 129 | 199 | 283 | — | 427 | 480 | 555 | 618 | 66.4 | 65.5 | 64.8 | — | 61.2 | 59.7 | 58.3 | 56.4 |
| Comparative Catalyst 17 | 132 | 209 | 275 | 359 | — | 484 | 568 | 623 | 66.7 | 65.4 | 64.4 | 64.0 | — | 59.2 | 57.9 | 56.8 |
| Comparative Catalyst 18 | 127 | 213 | — | 345 | 433 | 489 | 547 | 628 | 65.1 | 65.0 | — | 61.8 | 60.6 | 58.4 | 57.2 | 55.1 |
| Comparative Catalyst 19 | 118 | 186 | — | — | 333 | 400 | 465 | 592 | 62.0 | 61.8 | — | — | 59.9 | 58.7 | 57.5 | 55.7 |
| Comparative Catalyst 20 | 133 | 204 | 288 | — | 437 | 490 | 564 | 625 | 67.6 | 66.8 | 65.7 | — | 61.4 | 59.7 | 57.1 | 55.4 |
| Comparative Catalyst 21 | 116 | 196 | — | 323 | 380 | 447 | 505 | 573 | 60.9 | 60.5 | — | 57.6 | 55.9 | 55.2 | 52.9 | 53.0 |
| Comparative Catalyst 22 | 104 | 146 | 196 | — | 278 | 322 | 361 | 399 | 47.0 | 44.0 | 41.7 | — | 36.9 | 35.9 | 34.0 | 32.5 |

Mn—Bi+various metal catalyst activity evaluation result (2)

TABLE 2

| Catalyst | Added Element <1> | | Added Element <2> | | Yield (%) | | Extrapolated Amount of HBD |
|---|---|---|---|---|---|---|---|
| | Added Element | Atomic Ratio (relative to manganese) | Added Element | Atomic Ratio (relative to manganese) | after 2 days | after 9 days | Production (g/g-cat) (day 2 to day 9) Yield: 55%[1] |
| Catalyst 1 | Bi | 1.1% | Y | 1.1% | 66.55 | 59.71 | 999 |
| Catalyst 2 | Bi | 1.1% | V | 1.1% | 66.24 | 60.08 | 1029 |
| Comparative Catalyst 1 | Bi | 1.1% | — | — | 61.65 | 54.40 | 556 |
| Comparative Catalyst 2 | Bi | 1.1% | La | 1.1% | 63.57 | 53.94 | 576 |
| Comparative Catalyst 3 | Bi | 1.1% | Ce | 1.1% | 56.86 | 40.92 | 164 |
| Comparative Catalyst 4 | Bi | 1.1% | Er | 1.1% | 63.69 | — | 732 |
| Comparative Catalyst 5 | Bi | 1.1% | Yb | 1.1% | 64.88 | 57.18 | 740 |
| Comparative Catalyst 6 | Bi | 1.1% | Ti | 1.1% | 54.65 | 43.31 | — |
| Comparative Catalyst 7 | Bi | 1.1% | Zr | 1.1% | 60.05 | 55.08 | 678 |
| Comparative Catalyst 8 | Bi | 1.1% | Re | 1.1% | 65.52 | — | 789 |
| Comparative Catalyst 9 | Bi | 1.1% | Fe(II) | 1.1% | 61.85 | — | 551 |
| Comparative Catalyst 10 | Bi | 1.1% | Fe(III) | 1.1% | 63.66 | 54.56 | 595 |
| Comparative Catalyst 11 | Bi | 1.1% | Co | 1.1% | 61.71 | 50.49 | 397 |
| Comparative Catalyst 12 | Bi | 1.1% | Ni | 1.1% | 64.44 | 55.64 | 649 |
| Comparative Catalyst 13 | Bi | 1.1% | Cu | 1.1% | 33.10 | — | — |
| Comparative Catalyst 14 | Bi | 1.1% | Ag | 1.1% | 68.19 | 55.51 | 652 |
| Comparative Catalyst 15 | Bi | 1.1% | Zn | 1.1% | 66.54 | 56.61 | 702 |
| Comparative Catalyst 16 | Bi | 1.1% | Al | 1.1% | 66.37 | 56.44 | 712 |
| Comparative Catalyst 17 | Bi | 1.1% | Al | 1.1% | 66.73 | 56.82 | 712 |
| Comparative Catalyst 18 | Bi | 1.1% | Ga | 1.1% | 65.09 | 55.14 | 662 |
| Comparative Catalyst 19 | Bi | 1.1% | In | 1.1% | 62.00 | 55.71 | 656 |
| Comparative Catalyst 20 | Bi | 1.1% | Tl | 1.1% | 67.58 | 55.42 | 662 |

TABLE 2-continued

| Catalyst | Added Element <1> | | Added Element <2 | | Yield (%) | | Extrapolated Amount of HBD |
|---|---|---|---|---|---|---|---|
| | | Atomic Ratio | | Atomic Ratio | after | after | Production (g/g-cat) (day 2 |
| | Added Element | (relative to manganese) | Added Element | (relative to manganese) | 2 days | 9 days | to day 9) Yield: 55%[1] |
| Comparative Catalyst 21 | Bi | 1.1% | Sn | 2.0% | 60.94 | 52.95 | 443 |
| Comparative Catalyst 22 | Bi | 1.1% | W | 1.1% | 6.61 | — | — |

[1]Amount of HBD production at a yield 55% on the primary line derived from the amount of HBD production and the yield thereof from day 2 to day 9.

(2-1) Preparation of Catalyst
Catalyst 3

62.96 g (0.398 mol) of potassium permanganate was dissolved in 217.54 ml of water, and while the resulting liquid was kept stirred at 85° C., immediately added thereto was a liquid that had been prepared by dissolving 56.36 g (0.333 mol) of manganese sulfate monohydrate and 1.56 g (0.007 mol) of vanadium(IV) oxysulfate 3.7-hydrate in 215.48 ml of water followed by further mixing the solution with 99.94 g (1.019 mol) of concentrated sulfuric acid and kept at 55° C. After the addition, the reaction mixture was ripened by stirring at 70° C. for 2 hours, and further at 90° C. for 4 hours; and thereafter a liquid prepared by suspending 0.48 g (0.001 mol) of bismuth(III) oxide in 440 ml of water was immediately added to the reaction mixture. After this was stirred at room temperature for 30 minutes, the formed precipitate was taken out through filtration and washed until the electroconductivity of the wash waste could reach 300 μS/cm, thereby giving a precipitate cake.

The obtained cake was molded through an extrusion molding machine (cylinder diameter 35 mmϕ, nozzle diameter 1.5 mmϕ×24 holes, aperture 4.4%, hydraulic system) and dried with a stationary drier at 110° C. for 16 hours thereby giving about 60 g of a molded catalyst with a size of 1.0 mmϕ×3 to 7 mm.

Catalyst 4

A catalyst produced in the same manner as that for the catalyst 3 except that the amount of vanadium(IV) oxysulfate 3.7-hydrate was 0.779 g (0.003 mol) and that of bismuth(III) oxide was 0.950 g (0.002 mol).

Catalyst 5

A catalyst produced in the same manner as that for the catalyst 3 except that the amount of vanadium(IV) oxysulfate 3.7-hydrate was 0.390 g (0.002 mol) and that of bismuth(III) oxide was 1.90 g (0.004 mol).

Comparative Catalyst 23

A catalyst produced in the same manner as that for the catalyst 3 except that the amount of vanadium(IV) oxysulfate 3.7-hydrate was 1.91 g (0.008 mol) but that bismuth(III) oxide was not added.

(2-2) Determination of Acetone Cyanhydrin Hydration Performance

Catalysts 3 to 5, Comparative Catalyst 23

According to the same method as in (1-2), the amount of HBD produced before the HBD yield lowered to 55% was determined.

The atomic ratio of bismuth/manganese, vanadium/manganese, (bismuth+vanadium)/manganese, bismuth/(bismuth+vanadium) in each catalyst, and the amount of HBD production (g/g-cat) are shown in Table 3.

Mn—Bi—V Various Composition Catalyst Activity Evaluation Result (1)

TABLE 3

| Catalyst | Bi/Mn % | V/Mn % | (Bi + V)/Mn % | Bi/(Bi + V) % | Amount of HBD Production (g/g-cat) |
|---|---|---|---|---|---|
| Comparative Catalyst 23 | 0 | 1.1 | 1.1 | 0 | 253 |
| Catalyst 3 | 0.3 | 0.9 | 1.2 | 25 | 1220 |
| Catalyst 4 | 0.6 | 0.5 | 1.0 | 55 | 1729 |
| Catalyst 5 | 1.1 | 0.2 | 1.3 | 85 | 818 |
| Comparative Catalyst 1 | 1.1 | 0 | 1.1 | 100 | 578 |

From the results in Table 3 where the atomic ratio of (bismuth+vanadium)/manganese was fixed at about 1.2%, it is known that the amount of production is especially high when the atomic ratio of bismuth/(bismuth+vanadium) is from 25% to 85%.

(3-1) Preparation of Catalyst
Catalyst 6

A catalyst produced in the same manner as that for the catalyst 3 except that the amount of bismuth(III) oxide was 1.90 g (0.004 mol).

Comparative Catalyst 24

A catalyst produced in the same manner as that for the catalyst 3 except that the amount of vanadium(IV) oxysulfate 3.7-hydrate was 3.12 g (0.013 mol) but that bismuth(III) oxide was not added.

Comparative Catalyst 25

A catalyst produced in the same manner as that for the catalyst 3 except that vanadium(IV) oxysulfate 3.7-hydrate was not added and that the amount of bismuth(III) oxide was 2.85 g (0.006 mol).

(3-2) Determination of Acetone Cyanhydrin Hydration Performance

Catalyst 6, Comparative Catalysts 24 to 25

According to the same method as in (1-2), the amount of HBD produced before the HBD yield lowered to 55% was determined.

The atomic ratio of bismuth/manganese, vanadium/manganese, (bismuth+vanadium)/manganese, bismuth/(bismuth+vanadium) in each catalyst, and the amount of HBD production (g/g-cat) are shown in Table 4.

Mn—Bi—V Various Composition Catalyst Activity Evaluation Result (2)

TABLE 4

| Catalyst | Bi/Mn % | V/Mn % | (Bi + V)/Mn % | Bi/(Bi + V) % | Amount of HBD Production (g/g-cat) |
|---|---|---|---|---|---|
| Comparative Catalyst 24 | 0 | 1.8 | 1.8 | 0 | 175 |
| Catalyst 6 | 1.1 | 0.9 | 2.0 | 55 | 924 |
| Comparative Catalyst 25 | 1.7 | 0 | 1.7 | 100 | 481 |

From the results in Table 4 where the atomic ratio of (bismuth+vanadium)/manganese was fixed at about 2%, it is known that the amount of production is especially high when the atomic ratio of bismuth/(bismuth+vanadium) is 55%.

(4-1) Preparation of Catalyst

Catalyst 7

A catalyst produced in the same manner as that for the catalyst 3 except that the amount of vanadium(IV) oxysulfate 3.7-hydrate was 0.346 g (0.002 mol) and the amount of bismuth(III) oxide was 0.340 g (0.0007 mol).

Catalyst 8

A catalyst produced in the same manner as that for the catalyst 3 except that the amount of vanadium(IV) oxysulfate 3.7-hydrate was 0.779 g (0.003 mol) and the amount of bismuth(III) oxide was 0.950 g (0.002 mol).

Catalyst 9

A catalyst produced in the same manner as that for the catalyst 3 except that the amount of vanadium(IV) oxysulfate 3.7-hydrate was 2.25 g (0.010 mol) and the amount of bismuth(III) oxide was 2.21 g (0.005 mol).

Catalyst 10

A catalyst produced in the same manner as that for the catalyst 3 except that the amount of vanadium(IV) oxysulfate 3.7-hydrate was 3.12 g (0.013 mol) and the amount of bismuth(III) oxide was 2.85 g (0.006 mol).

(4-2) Determination of Acetone Cyanhydrin Hydration Performance

Catalysts 7 to 10

According to the same method as in (1-2), the amount of HBD produced before the HBD yield lowered to 55% was determined.

The atomic ratio of bismuth/manganese, vanadium/manganese, (bismuth+vanadium)/manganese, bismuth/(bismuth+vanadium) in each catalyst, and the amount of HBD production (g/g-cat) are shown in Table 5.

Mn—Bi—V Various Composition Catalyst Activity Evaluation Result (3)

TABLE 5

| Catalyst | Bi/Mn % | V/Mn % | (Bi + V)/Mn % | Bi/(Bi + V) % | Amount of HBD Production (g/g-cat) |
|---|---|---|---|---|---|
| Catalyst 7 | 0.2 | 0.2 | 0.4 | 50 | 735 |
| Catalyst 8 | 0.6 | 0.5 | 1.1 | 55 | 1729 |
| Catalyst 6 | 1.1 | 0.9 | 2.0 | 55 | 924 |
| Catalyst 9 | 1.3 | 1.3 | 2.6 | 50 | 631 |
| Catalyst 10 | 1.7 | 1.8 | 3.5 | 48 | 563 |

From the results in Table 5 where the atomic ratio of bismuth/(bismuth+vanadium) was fixed at about 50%, it is known that the amount of production is especially high when the atomic ratio of (bismuth+vanadium)/manganese is from 0.4% to 2.6%.

The invention claimed is:

1. An amide compound production catalyst for producing an amide compound through reaction of a nitrile compound and water, which comprises a manganese oxide catalyst containing bismuth and further containing yttrium or vanadium.

2. The amide compound production catalyst according to claim 1, wherein the atomic ratio of bismuth/manganese is from 0.001 to 0.1.

3. The amide compound production catalyst according to claim 1, wherein the atomic ratio of yttrium/manganese is from 0.001 to 0.1.

4. The amide compound production catalyst according to claim 1, wherein the atomic ratio of vanadium/manganese is from 0.001 to 0.1.

5. The amide compound production catalyst according to claim 1, wherein the atomic ratio of (bismuth+vanadium)/manganese is from 0.002 to 0.040.

6. The amide compound production catalyst according to claim 1, wherein the atomic ratio of bismuth/(bismuth+vanadium) is from 0.05 to 0.95.

7. A method for producing an amide compound, which comprises reacting a nitrile compound and water in a liquid phase in the presence of the amide compound production catalyst of claim 1.

8. The amide compound production method according to claim 7, wherein the nitrile compound is an acetone cyanhydrin.

9. A method for producing an amide compound, which comprises reacting a nitrile compound and water in a liquid phase in the presence of the amide compound production catalyst of claim 2.

10. A method for producing an amide compound, which comprises reacting a nitrile compound and water in a liquid phase in the presence of the amide compound production catalyst of claim 3.

11. A method for producing an amide compound, which comprises reacting a nitrile compound and water in a liquid phase in the presence of the amide compound production catalyst of claim 4.

12. A method for producing an amide compound, which comprises reacting a nitrile compound and water in a liquid phase in the presence of the amide compound production catalyst of claim 5.

13. A method for producing an amide compound, which comprises reacting a nitrile compound and water in a liquid phase in the presence of the amide compound production catalyst of claim 6.

* * * * *